(12) United States Patent
Proudlock et al.

(10) Patent No.: US 8,221,646 B2
(45) Date of Patent: Jul. 17, 2012

(54) DECONTAMINATION FORMULATIONS

(75) Inventors: Kevin Proudlock, Smethwick (GB); Amanda Stuart, Smethwick (GB); Norman Govan, Salisbury (GB); Steven James Mitchell, Salisbury (GB); Harry McEvoy, Salisbury (GB)

(73) Assignee: The Secretary of State for Defence (GB)

( * ) Notice: Subject to any disclaimer, the term of this patent is extended or adjusted under 35 U.S.C. 154(b) by 636 days.

(21) Appl. No.: 12/282,966

(22) PCT Filed: Mar. 15, 2007

(86) PCT No.: PCT/GB2007/000877
§ 371 (c)(1),
(2), (4) Date: Aug. 4, 2009

(87) PCT Pub. No.: WO2007/104971
PCT Pub. Date: Sep. 20, 2007

(65) Prior Publication Data
US 2010/0010284 A1    Jan. 14, 2010

(30) Foreign Application Priority Data
Mar. 15, 2006 (GB) .................. 0605157.7

(51) Int. Cl.
*A62D 3/00* (2007.01)
*C09K 3/00* (2006.01)
*A62D 3/30* (2007.01)

(52) U.S. Cl. ........ 252/186.1; 516/73; 516/76; 588/300; 588/401; 588/405

(58) Field of Classification Search .............. 252/186.1; 588/401; 516/73, 76
See application file for complete search history.

(56) References Cited

U.S. PATENT DOCUMENTS

| | | | |
|---|---|---|---|
| H366 H | 11/1987 | Seiders | |
| 5,681,805 A * | 10/1997 | Scheuing et al. | 510/277 |
| 5,712,237 A * | 1/1998 | Stevens | 510/291 |
| 6,085,839 A * | 7/2000 | Wyant et al. | 166/292 |
| 6,228,832 B1 * | 5/2001 | Kinscherf et al. | 510/417 |
| 6,369,009 B1 | 4/2002 | Machac, Jr. et al. | |
| 6,723,891 B1 | 4/2004 | Wagner et al. | |
| 6,743,828 B1 | 6/2004 | Katz et al. | |
| 2002/0142928 A1 | 10/2002 | MacHac, Jr. et al. | |
| 2005/0109981 A1 | 5/2005 | Tucker et al. | |

FOREIGN PATENT DOCUMENTS

| | | |
|---|---|---|
| EP | 0412475 | 2/1991 |
| JP | 2000-095893 | 4/2000 |
| JP | 2003-226757 | 8/2003 |
| WO | WO 98/53883 | 12/1998 |
| WO | WO 2005/076777 | 8/2005 |

OTHER PUBLICATIONS

Shell Chemicals, NEODOL 91-6 Data sheet; Oct. 2005.*
Kirk-Othmer; Encyclopedia of Chemical Technology, 3rd ed., vol. 22, p. 347; 1983.*

* cited by examiner

*Primary Examiner* — Peter F Godenschwager
(74) *Attorney, Agent, or Firm* — Dean W. Russell; Kristin W. Crall; Kilpatrick Townsend & Stockton LLP

(57) ABSTRACT

The present application is concerned with compositions for providing phase-stable microemulsion decontamination formulations for treating surfaces, and in particular for treating surfaces contaminated with chemical and/or biological warfare agents.

15 Claims, No Drawings

DECONTAMINATION FORMULATIONS

CROSS REFERENCE TO RELATED APPLICATIONS

This application is the U.S. national phase of International Application No. PCT/GB2007/000877 filed on Mar. 15, 2007 and published in English on Sep. 20, 2007 as International Publication No. WO 2007/104971 A1, which application claims priority to Great Britain Application No. 0605157.7 filed on Mar. 15, 2006, the contents of both of which are incorporated herein by reference.

This invention is concerned with compositions for use in decontamination formulations, and decontamination formulations for treatment of surfaces, and in particular surfaces contaminated with chemical and/or biological warfare agents.

Decontaminant formulations for chemical and biological warfare agents commonly comprise aggressive solvents, such as xylene and toluene, and aggressive decontamination reagents. Aggressive solvents are required to both solvate the warfare agents and to solvate the acrylic polymers that are often added to chemical warfare agents to encourage them to stick to surfaces. These formulations are environmentally unfriendly and often unsuitable for decontaminating sensitive surfaces and equipment. It is therefore desirable to develop effective decontamination formulations for chemical warfare agents and biological warfare agents that are less toxic, less harsh and more environmentally friendly. Decontaminant formulations which conform to the high NATO decontamination standards are also required.

The present invention generally aims to provide effective compositions and decontamination formulations which are less toxic, less harsh and more environmentally friendly, and decontamination formulations which conform to NATO decontamination standards.

Accordingly, in a first aspect, the present invention provides a composition for use in a decontamination formulation comprising at least one surfactant and at least one of dimethyl adipate, dimethyl glutamate, dimethyl succinate and an alkylene glycol alkyl ether whereby said composition provides a phase stable microemulsion when mixed with a water-based solvent.

In a preferred embodiment the composition provides a phase stable microemulsion when mixed with a water-based solvent and a decontamination reagent. However, in alternative embodiments the composition may further comprise a decontamination reagent, or the water-based solvent may comprise a decontamination reagent.

The decontamination reagent is preferably a reagent capable of decontaminating and/or deactivating chemical warfare agents and/or biological warfare agents. Suitable reagents include sodium percarbonate and magnesium monoperoxyphthalate.

As used herein, a phase stable microemulsion is one that is stable for at least 15 min, and preferably at least 30 min.

A microemulsion is particularly ideal for decontaminating chemical warfare agents as the presence of the organic based composition provides an environment for solubilising the agent and for dissolving any acrylic polymers, whilst the water-based solvent provides an environment for dissolving the reagent. Furthermore, microemulsions have large phase interfaces allowing for a rapid reaction between the agents and the decontamination reagent. Microemulsions however in general contain a high percentage of water which could provide a logistical burden, and thus a composition is provided which may be diluted in a water-based solvent at the point of use.

The water-based solvent is preferably water as may be provided by local supplies in the vicinity where decontamination is required, for example on a battlefield, thus reducing the need to transport large volumes of liquid. It has been shown that an impure water source, and even sea water, is generally a suitable water-based solvent.

Dimethyl adipate, dimethyl glutamate and dimethyl succinate are particularly good for dissolving the acrylic polymers known to be blended with chemical warfare agents. They also have an acceptable environmental and toxicity profile. Alkylene glycol alkyl ethers also possess these properties, but in addition produce the most stable emulsions in the presence of reactive peroxy compounds, often the choice of decontamination reagent for deactivating a chemical warfare agent. The alkylene glycol alkyl ether may for example be dipropylene glycol monomethyl ether, ethylene glycol monobutyl ether or diethylene glycol monobutyl ether.

The at least one surfactant enables a microemulsion to be formed. Examples of surfactants include alcohol ethoxylates, the cationic surfactant N-alkyl tallow trimethyl ammonium chloride (Noramium MS 50), and dodecylbenzene sulphonic acid (DDBSA), which may be neutralised with monoethanolamine or triethanolamine. The at least one surfactant preferably comprises an alcohol ethoxylate which enables emulsification of any water insoluble materials, such as oils or grease, that may protect chemical warfare agents. Various alcohol ethoxylates could be used having differing degrees of ethoxylation and differing chain length alcohols. The alcohol ethoxylate may be $C_9$-$C_{11}$ alcohol ethoxylate 6EO which offers good stability of the microemulsion in the presence of peroxy compounds.

In a preferred embodiment the composition forms a phase stable microemulsion comprising between 5% and 50% v/v of the composition, more preferably between 5% and 30% v/v of the composition, and most preferably about 20% v/v of the composition.

The composition preferably comprises a solvent containing at least two of dimethyl adipate, dimethyl glutamate and dimethyl succinate, and more preferably a solvent containing all three of dimethyl adipate, dimethyl glutamate and dimethyl succinate. In the embodiment comprising a solvent containing all three the relative percentages in the solvent are preferably of dimethyl adipate 10 to 25% v/v, dimethyl glutamate 55 to 65% v/v and dimethyl succinate 15 to 25% v/v. Such a solvent is the commercially available dibasic ester solvent (Dupont), an environmentally friendly alternative to harsher solvents. These percentage ranges provide a composition of low volatility which is thus useful in a wide range of environments as it does not evaporate too quickly, a problem known for products containing xylene and toluene. The relatively high flash point of compositions comprising a solvent containing all three of dimethyl adipate, dimethyl glutamate and dimethyl succinate enhances the safety aspects of the product with regard to ignition.

The composition preferably comprises, by weight, between about 10 to 60% alkylene glycol alkly ether, between about 20 to 35% of a solvent containing dimethyl adipate, dimethyl glutamate and dimethyl succinate, and between about 5 to 30% of an alcohol ethoxylate. The first solvent more preferably comprises between about 40 to 60% alkylene glycol alkyl ether.

In one embodiment the composition comprises, by weight, 20% $C_9$-$C_{11}$ alcohol ethoxylate 6EO, 50% dipropylene glycol monomethyl ether, and 30% of a solvent containing dimethyl adipate, dimethyl glutamate and dimethyl succinate.

In one embodiment the composition may further comprise a thickening agent. A thickened microemulsion will provide improved adherence to surfaces, especially vertical surfaces, increase retention time and enable decontamination to proceed on the contaminated surface as distinct from the surrounding environment. Suitable thickening agents include xanthan gum and Ultrez™ 10 carbomer. Thickening agents should be selected such to avoid inhibiting the activity of the decontamination reagent. For example a microemulsion comprising up to about 5% xanthan gum is suitable for use with the reagent sodium percarbonate and a microemulsion comprising up to about 2.5% Ultrez™ 10 carbomer is suitable for use with the reagent magnesium monoperoxyphthalate.

In further embodiments the composition may further comprise agents suitable for stabilisation of the decontamination reagent. For example agents such as hydrotropes and tall oil fatty acids based soaps are suitable for stabilising peroxy reagents such as sodium percarbonate and magnesium monoperoxyphthalate. Suitable hydrotropes include MONOTROPE™ 810 (Uniqema) which comprises 15-30% potassium salt of decanoic acid and 15-30% potassium salt of octanoic acid. Suitable tall oil fatty acids include tall oil fatty acid 1 (TOFA1) and tall oil fatty acid 25 (TOFA25).

In one embodiment the composition comprises, by weight, 40% diethylene glycol monobutyl ether, 29% of a solvent comprising dimethyl adipate, dimethyl glutamate and dimethyl succinate, 19.3% $C_9$-$C_{11}$ alcohol ethoxylate 6EO, 3.5% TOFA1, 1.2% of a 99% triethanolamine solution and 7% MONOTROPE™ 810. This composition forms a phase stable emulsion when diluted to 20% v/v with the second water-based solvent, in the presence of either 5% sodium percarbonate or 5% magnesium monoperoxyphthalate as the decontamination reagent. Tests have shown the final decontamination formulations to be capable of thorough decontamination of surfaces containing chemical warfare agents such as mustard (bis-(2-chloroethyl)sulphide, V nerve agents and G nerve agents, and biological warfare agents, to NATO decontamination standards.

In a second aspect, the present invention provides a decontamination formulation comprising a composition of the first aspect, a water-based solvent and a decontamination reagent whereby the decontamination formulation is a phase stable microemulsion.

The decontamination formulation preferably comprises between 5% and 50% v/v of the composition, more preferably between 5% and 30% v/v of the composition, and most preferably about 20% v/v of the composition.

Suitable decontamination reagents include peroxy reagents such as sodium percarbonate and magnesium monoperoxyphthalate.

In a third aspect, the present invention provides a decontamination kit comprising a composition of the first aspect and a decontamination reagent.

The decontamination kit may further comprise a water-based solvent and/or apparatus means for producing and/or dispensing a phase-stable microemulsion.

In a fourth aspect, the present invention provides decontamination formulations of the second aspect and decontamination kits of the third aspect for treating surfaces.

The decontamination formulations and decontamination kits are preferably for treating surfaces contaminated with chemical warfare agents and/or biological warfare agents. The chemical warfare agents include sulfur mustard, V nerve agents and G nerve agents. Surfaces may be the surfaces of instrumentation, vehicles and clothing.

In a fifth aspect, the present invention provides a method for decontaminating a surface to remove a toxic chemical, said method comprising applying a decontamination formulation of the second aspect to a surface.

EXAMPLES

Compositions comprising either dibasic ester solvent (ESTA) and/or dipropylene glycol monomethyl ether were identified as good solvents for forming phase stable microemulsions, when diluted with a water-based solvent, suitable for solvating chemical warfare agent simulants. These solvents are also capable of dissolving the acrylic polymers known to be blended with chemical warfare agents. ESTA comprises dimethyl adipate (10 to 25% v/v), dimethyl glutamate (55 to 65% v/v) and dimethyl succinate (15 to 25% v/v). It was also shown that any of the three solvents alone could be used in forming a phase stable microemulsion.

Initial compositions comprised at least one of the above mentioned solvents and a surfactant ($C_9$-$C_{11}$ alcohol ethoxylate 6EO) which when diluted (20% v/v) in water formed a phase stable microemulsion. The compositions diluted (20% v/v) in water, were then assessed in three tests, a solvation test (test 1), a soak test (test 2) and a spray test (test 3), with a number of chemical warfare agent simulants, methyl salicylate (MS), thickened MS (TMS), triethyl phosphate (TEP), thickened TEP (TTEP), tripropyl phosphate (TPP) and thickened TPP (TTPP). Each composition has properties suitable for use as the organic phase of a decontamination microemulsion.

Test 1—Solvation Capacity

Chemical warfare agent simulant is added to diluted composition (formulation) dropwise whilst stirring until the capacity of the formulation is reached, i.e. until the solution phase separates or the simulant is no longer taken up into solution. The capacity is calculated, and the experiment repeated for each simulant.

Test 2—Soak Test

Chemical warfare agent simulant is added (5×2 µl drops) to a small glass plate (2×2 cm) of known weight and left in contact with the plate for 1 h. The plate plus simulant is then weighed. The plate is placed in a Petri dish on a level stable surface, and to this is added formulation (40 ml, or enough to cover the plate), carefully pouring the formulation into the side of the Petri dish, away from the plate. The formulation is left to soak for 30 min. The plate is carefully removed from the Petri dish, dipped into water to rinse and then placed in a beaker containing iso-propyl alcohol (IPA) solution (50 ml), and left for 2 h. The IPA solution is agitated to encourage solvation. The IPA solution containing simulant is then analysed. The higher the percentage recovery of simulant in the IPA solution is proportional to, and corresponds to, a lower solubility and/or lower decontamination of the simulant by the formulation.

Test 3—Spray Test

Chemical warfare agent simulant is added (8×25 µl drops; 4×50 µl drops for TTEP and TTPP) to a large plate (10×16 cm) of known weight and left in contact with the plate for 1 h. The plate plus simulant is then weighed. The plate is mounted on a rig such to hold the plate in a vertical orientation, and formulation (50 ml) sprayed onto the plate. The volume delivered, the pressure of delivery (50 ml over 30 s), the distance of the spray head from the plate (40 cm) and the number of spray passes (30) must be consistent between tests. The plate is then left to soak for 30 mins. The plate is removed from the rig, dipped once in water to rinse, then placed in a solution of IPA (200 ml) for 2 h. The IPA solution is agitated to encourage salvation. The IPA solution containing simulant is then analysed. The higher the percentage recovery of simulant in the IPA solution is proportional to, and corresponds to, a lower solubility and/or lower decontamination of the simulant by the formulation.

Example 1

Compositions investigated were E7, E12, E21, E22, E23, E24 and composition A. The three tests were carried out with formulations comprising a 20% v/v dilution of each composition in water.

Compositions

Ingredients are recorded in g to make 1 l, unless otherwise noted. $^a$E7 and E21 were made with water replacing the methyl salicylate in the decontaminant for the purposes of tests 2 and 3 because methyl salicylate is one of the CW agent simulants to be solvated.

| E7 | |
|---|---|
| Uniqema Solvent | 255.4 |
| Water | 217.9 |
| Monoethanolamine | 111.8 (MEA) |
| Tall oil fatty acid | 107.4 (TOFA) |
| Di-propylene glycol mono methyl ether | 101.2 (DPM) |
| Alcohol ethoxylate $c_9$-$c_{11}$ OH 9 EO | 51 |
| Coco imidazoline betaine | 29.8 |
| Di propylene glycol | 29.8 (DPG) |
| Diethanolamine | 28.9 (DEA) |
| Pine oil | 15.5 |
| Methyl salicylate$^a$ | 10.6 |
| Butylated hydroxy toluene | 1 |

| E12 | |
|---|---|
| Water | 374 |
| Hydroxyethylenediamine triacetic acid (Na salt) | 50.7 |
| DPM | 51.1 |
| Dodecylbenzene sulphonic acid | 112.4 (DDBSA) |
| MEA | 57.9 |
| Alcohol ethoxylate $c_9$ 9EO | 75 |
| Uniqema solvent | 58.3 |
| Butylated hydroxy toluene | 1 |

| E21 | |
|---|---|
| Water | 277.2 |
| D'limonene | 259.2 |
| Di ethylene glycol mono butyl ether | 96 |
| MEA | 95 |
| TOFA | 91.7 |
| Alcohol ethoxylate $c_9$-$c_{11}$ OH 9 EO | 43.2 |
| DPG | 34.7 |
| DEA | 24.8 |
| Coco imidazoline betaine | 19.2 |
| Pine oil | 13 |
| Methyl salicylate$^a$ | 8.6 |
| Tolyl triazole | 1.9 |
| Butylated hydroxyl toluene | 1.0 |

| E22 | |
|---|---|
| Water | 603.9 |
| Alcohol ethoxylate $C_{12}$ OH 7 EO | 168.3 |
| Hexylene glycol | 128.7 |
| Solvesso 150 | 55 ($C_{10}$-$C_{11}$ Alkyl benzenes) |
| TOFA | 23.9 |
| Triethanolamine | |

| E23 | |
|---|---|
| Water | 607.5 |
| Iso paraffin | 108.2 |
| Solvesso 150 | 93.3 |
| DDBSA | 74.3 |
| Coconut diethanolamide | 44.8 |
| Propylene glycol n-butyl ether | 27.5 |
| Tri sodium phosphate | 27.5 |

| -continued | |
|---|---|
| DPM | 11.8 |
| MEA | 9.8 |
| Alcohol ethoxylate $C_{12}$-$C_{15}$ OH 2.5EO | 6.9 |
| Tolyl triazole | 3.9 |
| Sodium silicate | 2 |

| E24 | |
|---|---|
| Water | 448.4 |
| Sodium xylene sulphonate (30% aqueous solution) | 153 |
| Solvesso 150 | 104.3 |
| Di ethylene glycol mono butyl ether | 93.8 |
| DDBSA | 89 |
| Sodium tripoly phosphate | 20.9 |
| Sodium hydroxide (47%) | 27.47 |
| Alcohol ethoxylate $c_9$-$c_{11}$ OH 9 EO | 8.9 |
| Sodium silicate | 6.3 |
| Tolyl triazole | 4.2 |
| Ammonia | 2.1 |

| Composition A (percentage by weight; wt %) | |
|---|---|
| Dibasic ester solvent | 37 |
| Dipropylene glycol monomethyl ether | 22 |
| C9-11 alcohol ethoxylate, 6EO | 15 |

In test 1 all seven formulations readily solvated 1.5% (w/v) TEP. The majority of formulations were able to solvate 1.8% TEP, except for E7 and composition A which solvated 1.1% TPP. MS was the most difficult unthickened simulant to solvate, with E24 solvating more than 0.7%, but all other formulations were less than 0.3%. A white solid (possibly polymer thickener) appeared in all formulations after addition of 0.1% TTEP or TTPP to 50 ml of formulation. Only composition A was able to solvate TMS, though the formulation began to phase separate after addition of 0.2% TMS.

All TEP and TPP dosed plates in test 2 appeared clean when removed from the formulations after 30 min. Plates contacted with MS contained white drops where the colourless simulant had been dosed, however these appeared to detach when the plate was dipped in water to rinse the plate. The colourless thickened simulants TTEP, TTPP and TMS also produced white spots on the plates, but unlike MS did not appear to rinse off in the water. The analysis of the IPA solution used to extract any remaining simulant from the plate, calculated as % recovery of simulant, showed that the composition A based formulation removed most simulant from the plates, particularly for TMS In test 3, with the exception of diluted (20% v/v) composition A, all plates were completely dry within 10 min of applying the formulation. The plates sprayed with a formulation of composition A remained wet for longer than for all the other simulants, the majority of which ran off immediately and thus coverage of the plate for 30 min was not achieved. All plates dosed with MS, TEP or TPP appeared clean at the end of the 30 min soak/drain period. The thickened simulants were however clearly visible on all plates throughout the test, though after spraying the decontaminant did lose their colourless appearance. Rinsing the plates in water did not remove simulant. The TMS dosed plate sprayed with formulation of composition A had significantly less thickened simulant visible after 30 min, than using other formulations. The recovery of simulant from the plates after at the end of the test was generally much higher than for test 2.

Example 2

Improved Compositions and Formulations

Compositions Developed

The following compositions are all listed as percentage by weight (wt %), unless otherwise noted. b dibasic ester solvent contains 10-25% dimethyl adipate, 55-65% dimethyl glutarate and 15-25% dimethyl succinate; [c]decontamination formulations containing Carbopol™ Ultrez 10 are made by adding, with stirring, the Ultrez 10 and decontamination reagent to the water then finally adding the composition;

| F9 | |
|---|---|
| Dibasic ester solvent | 37 |
| Dipropylene glycol monomethyl ether | 22 |
| C9-11 alcohol ethoxylate, 6EO | 15 |
| DDBSA | 14 |
| Triethanolamine | 12 |

| F11 | |
|---|---|
| Dibasic ester solvent | 34 |
| Dipropylene glycol monomethyl ether | 20 |
| C9-11 alcohol ethoxylate, 6EO | 13.5 |
| DDBSA | 27 |
| Monoethanolamine | 5.5 |

| F12 | |
|---|---|
| Dibasic ester solvent | 30.3 |
| Dipropylene glycol monomethyl ether | 18 |
| DDBSA | 24.3 |
| Monoethanolamine | 4.9 |
| Noramium MS 50 | 22.5 (NMS50) |

| F20 | |
|---|---|
| Dibasic ester solvent | 30.7 |
| THF alcohol | 18.9 |
| C9-11 alcohol ethoxylate, 6EO | 12.2 |
| DDBSA | 17.3 |
| Monoethanolamine | 3.8 |
| NMS50 | 17.1 |

| F21 | |
|---|---|
| Dibasic ester solvent | 28.6 |
| Ethyl diglycol | 17 |
| DDBSA | 26.8 |
| Monoethanolamine | 6.3 |
| NMS50 | 21.3 |

| F22 | |
|---|---|
| Dibasic ester solvent | 28.6 |
| Butyl glycol | 17 |
| DDBSA | 26.8 |
| Monoethanolamine | 6.3 |
| Noramium MS 50 | 21.3 |

| F23 | |
|---|---|
| Dibasic ester solvent | 28.6 |
| Diethylene glycol monobutyl ether | 17 |
| DDBSA | 26.8 |
| Monoethanolamine | 6.3 |
| NMS50 | 21.3 |

| F24 | |
|---|---|
| Dibasic ester solvent | 28.5 |
| Diethylene glycol monobutyl ether | 12.9 |
| Monoethanolamine | 12.7 |
| Tall oil fatty acid (TOFA25) | 12.3 |
| Isotridecanol, 5EO | 20.0 |
| Di propylene glycol | 4.6 |
| Diethanolamine | 3.3 |
| Cocoimidazolinbetaine | 2.6 |
| Pine oil | 1.7 |
| Methyl salicylate | 1.2 |
| Sodium tolytriazole | 0.2 |

| F31 | |
|---|---|
| Dibasic ester solvent | 30 |
| Dipropylene glycol monomethyl ether | 50 |
| C9-11 alcohol ethoxylate, 6EO | 20 |
| Thickener Carbopol™ Ultrez 10[c] (2.75%) (Noveon Europe) is then added to the microemulsion (20% v/v dilution of composition in water). | |

| F32 | |
|---|---|
| Dibasic ester solvent | 30 |
| Diethylene glycol monobutyl ether | 50 |
| C9-11 alcohol ethoxylate, 6EO | 20 |
| Thickener Carbopol™ Ultrez 10[c] (2.5%) is then added to the microemulsion (20% v/v dilution of composition in water). | |

| F33 | |
|---|---|
| Dibasic ester solvent | 30 |
| Ethylene glycol monobutyl ether | 50 |
| C9-11 alcohol ethoxylate, 6EO | 20 |
| Thickener Carbopol™ Ultrez 10[c] (2.5%) is then added to the microemulsion (20% v/v dilution of composition in water). | |

| Modified F12 | |
|---|---|
| dibasic ester solvent | 28.2 |
| dipropylene glycol monomethyl ether | 16.8 |
| DDBSA | 22.3 |
| monoethanolamine | 7.1 |
| C9-11 alcohol ethoxylate 6EO | 4.6 |
| NMS50 | 21.0 |

| F32/F12 hybrid | |
|---|---|
| dibasic ester solvent | 22.3 |
| diethylene glycol monobutyl ether | 31.5 |
| C9-11 alcohol ethoxylate 6EO | 7.4 |
| DDBSA | 14.8 |
| MEA | 6.4 |
| NMS50 | 10.4 |
| Thickener Carbopol™ Ultrez 10[c] (2.5%) is then added to the microemulsion (20% v/v dilution of composition in water). | |

| F36 | |
|---|---|
| diethylene glycol monobutyl ether | 40 |
| dibasic ester solvent | 24 |
| C9-11 alcohol ethoxylate 6EO | 16 |
| (20% w/v KZAN in monopropylene glycol) | 20 |
| Where KZAN[d] is Kelzan S™ (fCPKelco); a xanthan gum | |

| F48 | |
|---|---|
| diethylene glycol monobutyl ether | 40 |
| dibasic ester solvent | 30 |
| C9-11 alcohol ethoxylate 6EO | 20 |
| soap (2.54 TOFA25:1 99% TEA) | 10 |
| Where TOFA25 is tall oil fatty acid with 25-30% rosin acids | |

| F49 | |
|---|---|
| diethylene glycol monobutyl ether | 50 |
| dibasic ester solvent | 30 |
| C9-11 alcohol ethoxylate 6EO | 10 |
| soap (2.54 TOFA25:1 99% TEA) | 10 |

| F50 | |
|---|---|
| diethylene glycol monobutyl ether | 50 |
| dibasic ester solvent | 25 |
| C9-11 alcohol ethoxylate 6EO | 25 |

| F51 | |
|---|---|
| diethylene glycol monobutyl ether | 50 |
| dibasic ester solvent | 20 |
| C9-11 alcohol ethoxylate 6EO | 30 |

| F52 | |
|---|---|
| diethylene glycol monobutyl ether | 50 |
| dibasic ester solvent | 22 |
| C9-11 alcohol ethoxylate 6EO | 28 |

| F53 | |
|---|---|
| diethylene glycol monobutyl ether | 40 |
| dibasic ester solvent | 29.9 |
| C9-11 alcohol ethoxylate 6EO | 20 |
| TOFA1 | 3.35 |
| 99% TEA | 1.7 |
| MONOTROPE™ 810 | 5.05 |

| F54 | |
|---|---|
| diethylene glycol monobutyl ether | 40 |
| dibasic ester solvent | 29 |
| C9-11 alcohol ethoxylate 6EO | 19.3 |

-continued

| TOFA1 | 3.5 |
|---|---|
| 99% TEA | 1.2 |
| MONOTROPE ™ 810 | 7 |
| Where MONOTROPE ™ 810 is 15-30% potassium salt of decanoic acid and 15-30% potassium salt of octanoic acid (Uniqema) | |
| F55 (foam formulation) | |
| diethylene glycol monobutyl ether | 45 |
| C9-11 alcohol ethoxylate 6EO | 18 |
| dibasic ester solvent | 30 |
| sodium alkyl ethoxy sulphate 3EO | 2 |
| alkyl dimethylamine oxide | 5 |

Following on from the favourable results for composition A in the three tests in Example 1 improvements to this composition were investigated. Composition A comprises a dibasic ester solvent (30 wt %), containing 10-25% dimethyl adipate, 55-65% dimethyl glutarate and 15-25% dimethyl succinate, dipropylene glycol monomethyl ether (50 wt %) and $C_9$-$C_{11}$ alcohol ethoxylate, 6EO (20 wt %). The improvements focussed on increasing solvation capacity, thickening of both the composition and the diluted (20% v/v) composition in water and the stability of decontamination reagents, especially sodium percarbonate and magnesium monoperoxyphthalate, in the diluted (20% v/v) composition in water.

The solvation properties were improved by increasing the percentage of the dibasic ester solvent, at the expense of the dipropylene glycol monomethyl ether, in composition A. This however caused instability of the 20% v/v dilution in water. The stability was however restored by incorporating the surfactant dodecylbenzene sulphonic acid into the composition and neutralising with either monoethanolamine (F11) or triethanolamine (F9). The alcohol ethoxylate was then removed as it found that it was no longer required for stability of the microemulsion. Thickening of the final formulation (20% v/v of composition in water) was achieved by adding cationic surfactant Noramium MS 50 (N-alkly tallow trimethyl ammonium chloride in IPA/water) to the composition (F12). The composition F12 therefore comprised the dibasic ester solvent (30.3 wt %), dipropylene glycol monomethyl ether (18%), dodecylbenzene sulphonic acid (24.3 wt %), monoethanolamine (4.9 wt %) and Noramium MS 50 (22.5 wt %).

A formulation of F12 diluted (20% v/v) in water was then compared with a formulation of composition A diluted (20% v/v) in water in tests 1 to 3 with TMS, TTEP and TTPP. The formulation of F12 was observed to cling to the vertical test plates of test 3 for the entire 30 minute soak period. There appeared to be less simulant on the plates after the 30 min period than when using previous formulations. Analysis of the final IPA solution showed that although removal of TMS by the formulation of F12 was not as good as that for the formulation of composition A, the removal of TTEP and TTPP was greatly improved.

It is desirable that the compositions are able to form phase stable microemulsions in fresh and sea water. Decontamination formulations of composition A, F12, F9, F11, and further compositions (F20, F21, F23 and F24) were capable of producing a phase stable microemulsion when diluted (20% v/v) in sea water. Only one composition (F22) did not produce a phase stable microemulsion when diluted (20% v/v) with sea water. Composition F20 was the only composition to retain enough viscosity to prevent complete run off from the vertical plate in test 3.

The stability of decontamination reagents with F12 was also investigated, especially the stability of sodium percarbonate and magnesium monoperoxyphthalate in the diluted (20% v/v) composition in water. Addition of 5% magnesium monoperoxyphthalate to diluted F12 (20% v/v) in water caused phase separation, however a phase stable microemulsion was produced with a 25% v/v dilution of F12 in 1% sodium polymetaphosphate. A phase stable microemnulsion could however also be produced with a composition comprising 5% alcohol ethoxylate (modified F12 composition). A formulation of modified F12 diluted in tap water is capable of providing a phase stable microemulsion with both 5% magnesium monoperoxyphthalate and 5% sodium percarbonate. Modified F12 also has a stability of 30 min at room temperature when made with sea water, and with addition of 5% magnesium monoperoxyphthalate.

A variety of thickening agents was also investigated including Carbapol™ Ultrez 10 (Noveon Europe), Methocel™ K15-DGS-E hydroxypropyl methylcellulose (Dow Europe SA) and xanthan gum. Carbapol™ Ultrez 10 added to composition A formed clumps which did not disperse, however addition of the thickener (3% w/v of microemulsion) to the water before, after or as a blend with reagent magnesium monoperoxyphthalate did create thickening, which increased greatly when composition A was added. In the absence of magnesium monoperoxyphthalate the increased viscosity was not generated when composition A was added. A formulation comprising 2.75% Carbapol™ Ultrez 10 gave the microemulsion the viscosity required to cling to vertical surfaces. When applied to a test 3 TMS contaminated vertical plate the formulation remained as a thick layer with a gel-like appearance on the surface for the entire 30 min, and did not appear to drag TMS down the plate. It did appear as though a large proportion of the TMS had dissolved in the formulation. The TMS recovered from the plates after decontamination was 17.5% and 24.2% (duplicate experiments), the lowest recovery and therefore best formulation, even though the pressure of application was lower, due to the viscosity. The increased viscosity was expected to increase the recovery of simulant from horizontal soak test plates, due to slower diffusion, however the TMS recovered from a test 2 plate after decontamination was 26.8%, which was in fact lower than for all previous formulations, other than that for diluted (20% v/v) composition A.

Compositions comprising diethylene glycol monobutyl ether (F32) or ethylene glycol monobutyl ether (F33) rather than dipropylene glycol mono methyl ether required only 2.5% Carbapol™ Ultrez 10 to thicken microemulsions. These formulations also removed more TMS from test 3 plates than the F31 based formulation. The highest recovery of TMS was 3.9%. The F32 based formulation was also able to solvate drops of TMS in test 1.

The amount of Carbapol™ Ultrez 10 in formulations of diluted (20% v/v) F32 plus 5% magnesium monoperoxyphthalate were varied from 1.2%, with a viscosity close to that of water, to 2.8%, which had to be poured over the plate as it was too thick to spray. The optimum level of thickener in presence of magnesium monoperoxyphthalate was found to be around 2.5%, which was also the amount found to give the formulation excellent cling properties to vertical surfaces.

Test 2 and test 3 were also carried out with formulations comprising various dilutions of F32. The viscosity was shown to reach a maximum with a 10% v/v dilution of F32 in water, with the viscosity decreasing as the dilution of F32 decreased. To counteract this effect, and allow the viscosity to remain constant, the percentage Carbapol™ Ultrez 10 was also varied. Thus, to a 40% v/v dilution of F32 was added a solution comprising the maximum concentration of thickener possible and magnesium monoperoxyphthalate (MMPA). All lower dilutions were then viscosity matched to this (Table 1).

Results showed that decrease in dilution of F32 did not proportionately increase the solvation of TMS.

TABLE 1

Decontamination formulations of F32 composition.

| Dilution of F32 (% v/v) | Water (ml) | F32 (ml) | MMPA (g) | Carbapol ™ Ultrez 10 (g) |
| --- | --- | --- | --- | --- |
| 20 | 80 | 20 | 5 | 2.000 |
| 25 | 75 | 25 | 5 | 2.375 |
| 30 | 70 | 30 | 5 | 2.750 |
| 35 | 65 | 35 | 5 | 3.125 |
| 40 | 60 | 40 | 5 | 3.500 |

Although Carbapol™ Ultrez 10 had the shortest wetting out time of all the available Carbapols and the thickened microemulsion could be formed in minutes, it was not desirable to have to add the thickener component separately as a powder. It was however shown that Carbapol™ Ultrez 10 could be introduced to F32 composition without forming clumps by gradually adding into the vortex of the stirring composition, and continuing to stir for several hours. The thickener wet out and therefore thickened the composition over several days, aided by the addition of 5% water. The maximum amount of thickener that could be included in the F32 composition to leave a pumpable composition was found to be 1.8% w/v, equivalent to 0.36% in the microemulsion (at 20% composition). However, at 20% v/v in water the viscosity of the microemulsion did not appear to be significantly greater that that of unthickened formulation, and addition of magnesium monoperoxyphthalate caused phase separation. The phase separation could however be prevented by using a solution of 0.5% citric acid in place of water to make the microemulsion.

When the microemulsion was made by adding Carbapol™ Ultrez 10 to the water only minutes before adding the F32 composition the thickener had not wet out thoroughly, explaining why the microemulsion continued to thicken over several hours if left to stand and why such a large quantity of the thickener (2.5% in microemulsion) was required. By incorporating the Carbapol™ Ultrez 10 into the composition with the inclusion of water it was thought that less could be used as it would be fully wet out and therefore more effective.

F32 composition produces phase stable microemulsions with 5% magnesium monoperoxyphthalate. However, when sea water was used instead of tap water to form the microemulsion with magnesium monoperoxyphthalate as the reagent the viscosity needed to allow it to cling to surfaces was not achieved and large amounts of foam were produced. Furthermore, replacing magnesium monoperoxyphthalate with sodium percarbonate or buffer causes the Carbapol™ Ultrez 10 tap water solution to form a gel which rapidly loses structure upon F32 composition addition. In an attempt to gain the solubility properties of F32 and the stability properties of modified F12, a hybrid of the two was formed (F32/F12 hybrid). The increased surfactant level of the hybrid formulation compared with F32 did not improve the stability in the presence of sea water, or sodium percarbonate.

Comparative stability tests were carried out at room temperature. Formulations comprising modified F12, Ultrez 10 thickened F32 and F32/F12 hybrid all appeared to have the necessary short term stability in the presence of 5% magnesium monoperoxyphthalate. Of the three microemulsions made using tap water as the major phase, only the modified F12 based formulation remained stable when 5% sodium percarbonate was added as the reagent. With the major phase as sea water, in the presence of 5% magnesium monoperoxyphthalate, modified F12 appears to be the most stable of the three. Both the F32/F12 hybrid and F32 microemulsions began to phase separate after 30 min with sodium percarbonate as the decontamination reagent and sea water as the aqueous phase. Modified F12 appeared to remain as one phase for the first 30 minutes but phase separated shortly after.

Xanthan gum was identified as a potential alternative to Carbapol™ Ultrez 10 as thickener, in particular KZAN (Kelzan S™; CPKelco). A dispersion of KZAN in monopropylene glycol (20% w/v) was added to F32 composition (20% w/w) to give a composition (F36) that thickened immediately when diluted (20% v/v) in water, and was stable with 5% magnesium monoperoxyphthalate. The result was therefore 0.8% thickener in the microemulsion, significantly less than the 2.5% Carbapol™ Ultrez 10 required, and it would not need to be supplied/added to the decontaminant as a separate powder. The KZAN settled to the bottom of the formulation composition on standing but readily re-dispersed by stirring or shaking. Adding the KZAN directly to the F32 composition (3.4% w/w) gave a dispersion of the thickener which settled on standing and, once re-dispersed, diluted to 20% v/v in water to give an immediately thickened microemulsion. 2.5% KZAN dispersed in the F32 composition, equivalent to 0.5% in the microemulsion, also gave a thickened formulation capable of clinging to vertical surfaces. Unlike Carbapol™ Ultrez 10 thickened microemulsions there was no increase in viscosity after standing but there was a temperature dependence on the system. At higher temperatures more KZAN was required to maintain viscosity. The formulations did not however thicken if magnesium monoperoxyphthalate was added to the water before the composition, though sodium percarbonate could be added to the water before or after the composition. Viscosity was lost at percentages of composition in the formulation of greater than 23%, and this was found to be due to the decrease in water content rather than the increase in the composition or any individual component of it.

The KZAN thickened formulation had greater stability in the presence of reagents than Carbapol™ Ultrez 10 thickened formulation. The microemulsions with sea water did not thicken, but did not separate within the first 30 min when stability is critical.

The solubility of TMS in the xanthan thickened formulation was investigated using test 2 and test 3. The formulation clung to the surface of the vertical test plates of test 3 for the 30 min soak. The recovery of TMS from the plates after decontamination with xanthan thickened microemulsions was much greater than comparable results using unthickened formulation or Ultrez 10 thickened microemulsions (with the exception of test 3 using unthickened formulation where run-off is an issue).

Soak tests using TMS were completed using varying amounts of KZAN thickener to find out if the negative impact on solubility began at a threshold level. The tests showed that TMS removal by the formulation was higher when less that 1.5% KZAN (0.3% in microemulsion) was used. This level did not however thicken the formulation sufficiently to allow vertical test plates to remain covered for 30 min. Without thickener the F32 based microemulsion phase separated immediately upon addition of 5% sodium percarbonate. The proportions of diethylene glycol monobutyl ether, dibasic ester solvent and $C_9$-$C_{11}$ alcohol ethoxylate 6EO in the composition were varied and the stability determined (Table 2).

TABLE 2

Modifications of F32 composition, and effect on decontamination formulations comprising a 20% v/v dilution of composition plus sodium percarbonate.

| Glycol (%) | Basic ester solvent (%) | Ethoxylate (%) | Microemulsion stability to sodium percarbonate |
|---|---|---|---|
| 50 | 30 | 20 | Phase separates with 3% |
| 45 | 30 | 25 | Phase separates with 4% |
| 55 | 30 | 15 | Phase separates immediately with 4% |
| 55 | 25 | 20 | Stable with 4%, phase separates with 5% |
| 50 | 25 | 25 | Stable with 4%, phase separates with 5% |
| 50 | 20 | 30 | Stable with 5% |
| 45 | 25 | 30 | Phase separates with 5% |

The optimum composition for stabilising sodium percarbonate was therefore 50% diethylene glycol monobutyl ether, 20% dibasic ester solvent and 30% $C_9$-$C_{11}$ alcohol ethoxylate 6EO (F51). It was also found that a soap comprising TOFA25 (tall oil fatty acid with 25-30% rosin acids) and triethanolamine (F48; F49) could provide stability in the presence of 5% sodium percarbonate. None of the F32, F48 or F49 based microemulsions (20% v/v) appeared to phase separate within the first 3 h of standing when magnesium monoperoxyphthalate was added to them.

Xanthan gum increased the viscosity of the soap containing formulations as expected until magnesium monoperoxyphthalate was added and the thickening effect was lost. The formulation did not therefore cling to vertical test plates long enough for TMS to be solubilised. The viscosity was however retained in the presence of magnesium monoperoxyphthalate when the microemulsion was made with 15% v/v of composition rather than 20% v/v. The microemulsions did however appear to retain more viscosity when the TOFA25 soap was replaced by a TOFA1 (tall oil fatty acid 1) comprising soap. Carbapol™ Ultrez 10 thickener worked as well when soap was present as it did without, as when combined with F32.

With 5% sodium percarbonate present the soap containing microemulsion had a pH of 9.5. Addition of sodium carbonate to raise this pH, to increase the reactivity of the formulation, caused phase separation. This was however cleared to form one stable phase by a small addition of hydrotrope. Monotrope™ 810 (Uniquema), a blend of potassium salts of octanoic acid and decanoic acids, was chosen to incorporate into the compositions as less was required than either the phosphate ester potassium salt or Monotrope™ 1620 alkyl polysaccharide. The inclusion of Monotrope™ 810 within the compositions resulted in the soap content being halved (F53 and F54) and the stability of 20% v/v dilutions with sodium percarbonate retained.

Test 2 was performed using unthickened formulations to assess the effect of compositions F32, F48, F49, F51 and F53 on the solubility of TMS (Table 3).

TABLE 3

Solubility of TMS in test 2.

| Composition (20% v/v dil. in water) | Difference from F32 composition | Test 2, % TMS recovery | Test 2, % TMS recovery - rpt |
|---|---|---|---|
| F32 | | 15.9 | 12.8 |
| F48 | 10% soap replacing glycol | 17.6 | 15.2 |
| F49 | 10% soap replacing alcohol ethoxylate | 44.3 | 37.8 |
| F51 | 10% extra alcohol ethoxylate replacing dibasic ester solvent | 36.3 | 33.1 |
| F53 | 5% soap, 5% Monotrope™ 810 replacing glycol | 34.1 | 35.5 |

The F48 based formulation was therefore almost as efficient at removal of TMS as the unthickened F32 based formulation, suggesting that reducing the level of glycol in the formulation has little effect on solubility of chemical warfare agents. The other composition based formulations however had a much reduced solubility of TMS.

A decontamination formulation comprising a 20% v/v dilution of F54 in water was shown to have the solubility characteristics required to thoroughly decontaminate chemical warfare agent decontaminated surfaces (see Example 3). The F54 microemulsion did thicken with Carbapol™ Ultrez 10, when magnesium monoperoxyphthalate was present, though not to the same extent as the F32 based formulation. The incorporation of KZAN gave little thickening to the microemulsion, though when applied to a vertical surface a thin layer did cling. This could be improved by doubling the amount of KZAN in the composition to 5%.

Composition F54, which is F32 with the addition of soap and hydrotrope, is phase stable when diluted to 20%, and with the her addition of 5% magnesium monoperoxyphthalate or 5% sodium percarbonate. Magnesium monoperoxyphthalate is suitable for decontamination of mustard (bis-(2-chloroethyl)sulphide (sulfur mustard) and biological agents, whilst sodium percarbonate is suitable for decontamination of G nerve agents and V nerve agents. Composition F54 plus 5% xanthan gum thickener initially produces a viscous microemulsion upon addition of a sodium percarbonate solution. Added to water alone greater viscosity is observed which is largely retained on the addition of magnesium monoperoxyphthalate. The magnesium monoperoxyphthalate must be added to the composition After the water/F54/xanthan mix has thickened. The dilution of F54 can be thickened with Carbapol™ Ultrez 10 (2.5% in microemulsion, added to water with the active reagent prior to adding the composition); it does not give as much viscosity to the microemulsion as it does to F32. Unthickened F54 remains phase stable at room temperature for 30 min when diluted 20% v/v with sea water, with 5% magnesium monoperoxyphthalate. The microemulsions formed are environmentally benign.

A composition was developed with increased foaming properties and foam stability (F55). Comparisons with unthickened F32 based microemulsion were made by shaking in stoppered measuring cylinders and observing the amount of foam and stability. Incorporation of a small amount of thickener, for example 1% Ultrez 10 added to F32 composition, would also aid foam stability. Applying F32 unthickened based microemulsion as foam to test 3 plates resulted in high recoveries of TMS (32.5 and 34.1%). Although these recoveries would be expected to improve with specialist equipment, the foam would not give such a good contact with the surface to be decontaminated as a thickened formulation would.

Example 3

An evaluation of the performance of a decontamination formulation comprising a 20% v/v dilution of F54, and either 5% sodium percarbonate or 5% magnesium monoperoxyphthalate, with the chemical warfare agents sulfur mustard (bis(2-chloroethyl)sulphide; >99% purity) thickened by addition of 5% K125 methacrylate polymer (tHD); Nerve agent GD (O-pinacolyl methylphosphonofluoridate; >99% purity) thickened by addition of 5% K125 methacrylate polymer (tGD); Nerve agent VX (O-ethyl-S-2-(diisopropylaminoethyl)methylphosphonothiolate; >97% purity).

Experiments were performed with the decontamination formulations at 30° C. and dispensed from a hand held sprayer at approximately 100 ml min$^{-1}$. Initial experiments indicated that a spraying regime of two applications, each of 4 min, 15 min apart with a water rinse after 30 min would consistently result in thorough decontamination.

In each experiment three trays were used, with two sample plates (160×100 mm) in each tray. All three trays were treated identically to provide sufficient replicates to determine confidence limits. The decontaminant run-off plus water rinse (the effluent) was also analysed for residual intact agent. Flat polyurethane-painted plates were contaminated with equal volumes of tHD, tGD and VX resulting in nominal initial contamination densities of 1.25 µl cm$^{-2}$ (12.5 ml m$^{-2}$). The nominal 12.5 ml m$^{-2}$ corresponds with 12.6 g m$^{-2}$ for VX, 12.2 g m$^{-2}$ for tGD and 15.2 g m$^{-2}$ for tHD, after correction for the weight of thickener.

The experiments were conducted using two orientations of the plates, vertical and near-horizontal (5°). Near-horizontal orientation was chosen because a true horizontal orientation would result in the submergence of test surfaces with decontaminant, and thus would result in an artificially high contact time. It would also prevent the delivery of fresh decontaminant to the surface.

After decontamination and rinse the plates were removed for solvent extraction. Finally the trays were rinsed with solvent (ethyl acetate) after each session to capture and remove any remaining agent. Residual contamination was extracted from the plates using 200 ml of propan-2-ol solvent. Residual contamination was sampled from all decontaminat run-off and water rinse samples using liquid/liquid solvent extraction. A 1:1 volume of ethyl acetate was introduced and the sample shaken thoroughly. A sample of the solvent phase was then taken after the phases had been allowed to separate for 10 minutes. Quantitative CW agent analysis was performed using well established techniques on an Agilent 6890 series gas chromatograph with a flame photometric detector (FPD) and split/splitless/on column injection ports. The results of these laboratory tests are shown in Tables 4 to 6.

TABLE 4

Decontamination of thickened HD.

| % recovery tHD, vertical | | | % recovery tHD, near-horizontal (5%) | | |
|---|---|---|---|---|---|
| Tray 1 | Tray 2 | Tray 3 | Tray 1 | Tray 2 | Tray 3 |
| <0.02 | <0.02 | <0.02 | 0.20 | 0.21 | 0.069 |
| <0.02 | <0.02 | <0.02 | 0.026 | 0.041 | 0.018 |
| Mean <0.02 | | | Mean 0.094 (SD 0.088) | | |

TABLE 5

Decontamination of thickened GD

| % recovery tGD, vertical | | | % recovery tGD, near-horizontal (5%) | | |
|---|---|---|---|---|---|
| Tray 1 | Tray 2 | Tray 3 | Tray 1 | Tray 2 | Tray 3 |
| <0.003 | <0.003 | <0.003 | <0.003 | <0.003 | <0.003 |
| <0.003 | <0.003 | <0.003 | <0.003 | <0.003 | <0.003 |
| Mean <0.003 | | | Mean <0.003 | | |

TABLE 6

Decontamination of VX.

| % recovery VX, vertical | | | % recovery VX, near-horizontal (5%) | | |
|---|---|---|---|---|---|
| Tray 1 | Tray 2 | Tray 3 | Tray 1 | Tray 2 | Tray 3 |
| 0.042 | 0.043 | 0.028 | 0.061 | 0.011 | 0.055 |
| 0.010 | 0.22 | 0.028 | 0.011 | 0.07 | 0.061 |
| Mean 0.062 (SD 0.078) | | | Mean 0.045 (SD 0.028) | | |

The NATO criterion of <10 µg cm$^{-2}$ residual mustard agent for 'thorough' decontamination corresponds with <0.66% of the initial 15.2 g m$^{-2}$ used in these laboratory tests. The NATO criterion of <1 µg cm$^{-2}$ residual VX for 'thorough' decontamination corresponds with <0.079% of the initial 12.6 g m$^{-2}$. The conservatively assumed criterion of <1 µg cm$^{-2}$ residual GD for 'thorough' decontamination corresponds with <0.082% of the initial 12.2 g m$^{-2}$.

The results of the tests thus indicate that the regime of two 4 minute spray applications was likely to achieve consistent 'thorough' decontamination of thickened mustard and thickened GD. The results for VX were marginal, the mean of the results met the 'thorough' criterion but some individual results exceeded the permissible level.

It was also shown that a 20% v/v dilution of composition A with 5% sodium percarbonate achieved decontamination of VX. The concentration of percarbonate is crucial; in addition to the peroxy anion, at ≧5% percarbonate the true peroxycarbonate ion was also produced. Peroxycarbonate is an oxidative catalyst, which is likely to oxidise the sulfur atom of VX and enhance subsequent perhydrolysis.

Example 4

Biological agent simulant decontamination was performed with a decontamination formulation comprising a 20% v/v dilution of F54 plus 5% magnesium monoperoxyphthalate. Test plates consisted of 80×40 mm alurinium panels coated with a standard military polyurethane paint coating. The plates were prepared for the biological decontamination test by pipetting drops of an aqueous suspension of spores of *Bacillus atrophaeus* (BG) onto the surface, then allowing to dry in a class III biological safety cabinet. This process protects the test pieces from adventitious contamination, whilst preventing the spores from contaminating the laboratory. The spore suspension was standardised to give 3×10$^8$ spores per ml and applied at a level of 0.1 ml per test piece, giving a final load of approximately 3×10$^7$ spores per test piece. The final concentration of spores (nominally 9.4×10$^9$ spores m$^{-2}$) is substantially in excess of the NATO recommended "Essential" challenge level of 10$^9$ spores (1 mg) per square metro. Contaminated plates were mounted in the test rig in both the vertical and horizontal positions, and treated with two 4 minute applications of decontaminant, at intervals of 15 minutes, followed by a water rinse. The decontamination formulation was delivered using a Hozelock Polyspray sprayer. After treatment, the plates were quenched by suspending in 150 ml aliquots of Casein Peptone Lecithin Polysorbate Broth (Merck) in sample pots. Following a quenching soak of not less than 5 minutes, and not more than 1 hour, the samples were thoroughly mixed, and 1 ml aliquots removed. Serial dilutions were then prepared, in Trypcase Soya Broth (Biomerieux) and counted by the spread plate method on Trypcase Soya Agar (Biomerieux). The presence-absence test was then performed by incubating the remaining broth with test plates in situ. Agar plates and broths were both incubated for 3 days at 37° C. Samples of decontaminant effluent from the tests were collected, quenched at a dilution of 1/100 and similarly tested. The results of the tests are shown in tables 7 and 8.

TABLE 7

Decontamination of *Bacillus atrophaeus* (BG), horizontal orientation;
*probable artefact due to adventitious contamination

| Sample | Residual Viable Count per Plate | Pres/Abs Test |
|---|---|---|
| Plate 1 | $5 \times 10^{2}$* | A* |
| Plate 2 | nil | A |
| Plate 3 | nil | P (level of <500) |
| Plate 4 | nil | A |
| Plate 5 | nil | A |
| Plate 6 | nil | A |
| Control | c.$3 \times 10^{7}$ | |
| Effluent | nil | A |

TABLE 8

Decontamination of *Bacillus atrophaeus* (BG), vertical orientation

| Sample | Residual Viable Count per Plate | Pres/Abs Test |
|---|---|---|
| Plate 1 | nil | A |
| Plate 2 | nil | A |
| Plate 3 | nil | A |
| Plate 4 | nil | A |
| Plate 5 | nil | A |
| Plate 6 | nil | A |
| Control | c.$3 \times 10^{7}$ | |
| Effluent | nil | A |

The NATO 'Essential' requirement for decontamination of *Bacillus anthracis* is a residual contamination <1000 Colony Forming Units (CFU) m$^{-2}$ and the 'Desirable' requirement is <20 CFU m$^{-2}$. For the $3.2 \times 10^{-3}$ m$^2$ plates used in these tests, the 'Essential' level would equate to <3.2 CFU per plate, or in whole numbers, a total of 16 per 5 plates tested. The 'Desirable' level is not measurable on this test system. However, the fact that the tests were conducted at a level of initial contamination density which is an order of magnitude greater than the NATO 'Essential' level, and the large number of negative results from presence/absence tests carried out on both the intact test plates and the decontamination run-off, give a strong indication that this is a highly effective formulation. The positive result from the one horizontal sample was most probably contaminated and may therefore be disregarded. It can be seen from the above results that in both horizontal and vertical tests, the NATO 'Essential' level was met, and it may be inferred that the formulation has the potential to meet the 'Desirable' level.

The invention claimed is:

1. A composition for use in a decontamination formulation comprising between about 10% to about 60% of an alkylene glycol alkyl ether, between about 20% to about 35% of a solvent containing dimethyl adipate, dimethyl glutamate and dimethyl succinate, and between about 5% to about 30% of an alcohol ethoxylate whereby said composition provides a phase stable microemulsion when mixed with a second water-based solvent.

2. The composition of claim 1, wherein the composition provides a phase stable microemulsion when mixed with a second water-based solvent and a decontamination reagent.

3. The composition of claim 1, wherein the alcohol ethoxylate is $C_9$-$C_{11}$ alcohol ethoxylate 6EO.

4. The-composition of claim 1, wherein the phase stable microemulsion comprises between about 5% and about 30% v/v of the composition.

5. The composition of claim 4, wherein the phase stable microemulsion comprises about 20% v/v of the first solvent.

6. The composition of claim 1, in which relative percentages of dimethyl adipate, dimethyl glutamate and dimethyl succinate are between about 10% and about 25% v/v, between about 55% and about 65% v/v and between about 15% and about 25% v/v, respectively.

7. The composition of claim 1, comprising between about 40% to about 60% alkylene glycol alkyl ether.

8. The composition of claim 1, in which the alkylene glycol alkyl ether is dipropylene glycol monomethyl ether, ethylene glycol monobutyl ether or diethylene glycol monobutyl ether.

9. The composition of claim 1, further comprising a thickening agent.

10. The composition of claim 9, in which the thickening agent is a xanthan gum.

11. The composition of claim 1, further comprising a stabilization agent for stabilization of the decontamination reagent.

12. The composition of claim 11, in which the stabilization agent comprises a hydrotrope or a soap.

13. A decontamination formulation comprising the composition of claim 1, a water-based solvent and a decontamination reagent wherein the decontamination formulation is a phase stable microemulsion.

14. The decontamination formulation of claim 13 comprising about 20% v/v of the composition of claim 1.

15. The decontamination formulation of claim 13, in which the decontamination reagent is sodium percarbonate or magnesium monoperoxyphthalate.

* * * * *